United States Patent
Damle et al.

(10) Patent No.: US 12,239,834 B2
(45) Date of Patent: Mar. 4, 2025

(54) RETINAL PROSTHESES

(71) Applicants: Nanovision Biosciences, Inc., La Jolla, CA (US); The Regents of the University of California, Oakland, CA (US)

(72) Inventors: Samir Damle, San Diego, CA (US); Yu-Hsin Liu, San Diego, CA (US); Nicholas W. Oesch, Del Mar, CA (US); Yu-Hwa Lo, San Diego, CA (US)

(73) Assignees: NANOVISION BIOSCIENCES, INC., La Jolla, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 826 days.

(21) Appl. No.: 17/080,779

(22) Filed: Oct. 26, 2020

(65) Prior Publication Data
US 2021/0121685 A1    Apr. 29, 2021

Related U.S. Application Data

(60) Provisional application No. 62/926,411, filed on Oct. 25, 2019.

(51) Int. Cl.
*A61N 1/05*   (2006.01)
*A61N 1/08*   (2006.01)
(Continued)

(52) U.S. Cl.
CPC ............. *A61N 1/0543* (2013.01); *A61N 1/08* (2013.01); *A61N 1/36046* (2013.01); *H01L 27/14679* (2013.01)

(58) Field of Classification Search
None
See application file for complete search history.

(56) References Cited

U.S. PATENT DOCUMENTS 7,009,647 B1 *  3/2006  Kozlowski ........ H01L 27/14679
                                                    257/257
11,497,913 B1 * 11/2022  Shire ................... A61N 1/36046
(Continued)

FOREIGN PATENT DOCUMENTS

JP      H08222718    *  8/1996
WO   WO 2019/081562 A1   5/2019

OTHER PUBLICATIONS

Ben Ayed, H. et al. Toward an optoelectronic-based visual prosthesis: control unit design and validation. Analog Integr Circ Sig Process 98, 311-320 (2019). https://doi.org/10.1007/s10470-018-1294-2 (Year: 2019).*

(Continued)

*Primary Examiner* — Melanie R Tyson
*Assistant Examiner* — Yasniary De La Caridad Morales
(74) *Attorney, Agent, or Firm* — NovoTechIP International PLLC

(57) ABSTRACT

Optoelectronic retinal prostheses transduce light into electrical current for neural stimulation. A novel optoelectronic pixel architecture is presented comprising a vertically integrated photo junction field-effect-transistor (Photo-JFET) and neural stimulating electrode. Experimental measurements demonstrate that optically addressed Photo-JFET pixels utilize phototransistive gain to produce a broad range of neural stimulation current and can effectively stimulate retinal neurons in vitro. The compact nature of the Photo-JFET pixel can enable high resolution retinal prostheses with a theoretical visual acuity ~20/60 to help restore vision in patients with degenerative retinal diseases.

20 Claims, 6 Drawing Sheets

(51) Int. Cl.
*A61N 1/36* (2006.01)
*H01L 27/146* (2006.01)

(56) References Cited

U.S. PATENT DOCUMENTS

| | | | | |
|---|---|---|---|---|
| 2005/0131490 | A1* | 6/2005 | Palanker | A61F 2/02 |
| | | | | 607/57 |
| 2007/0241377 | A1 | 10/2007 | Gouscha | |
| 2012/0129301 | A1* | 5/2012 | Or-Bach | H01L 29/66833 |
| | | | | 438/129 |
| 2016/0114163 | A1* | 4/2016 | Franke | A61N 1/3756 |
| | | | | 607/135 |
| 2019/0216328 | A1* | 7/2019 | Buyuksahin | A61N 1/37217 |
| 2020/0054441 | A1* | 2/2020 | Birge | A61F 2/14 |

OTHER PUBLICATIONS

Definition of diode retrieved from Oxford Languages (Year: 2023).*
International Preliminary Report on Patentability for PCT/US2020/057423; dated Jan. 27, 2021; 6 pages.
Sohmyung Ha et al.: "Towards high-resolution retinal prostheses with direct optical addressing and inductive telemetry", Journal of Neural Engineering, Institute of Physics Publishing, Bristol, GB, vol. 13, No. 5, Aug. 16, 2016 (Aug. 16, 2016), p. 56008 (19 pages).

* cited by examiner

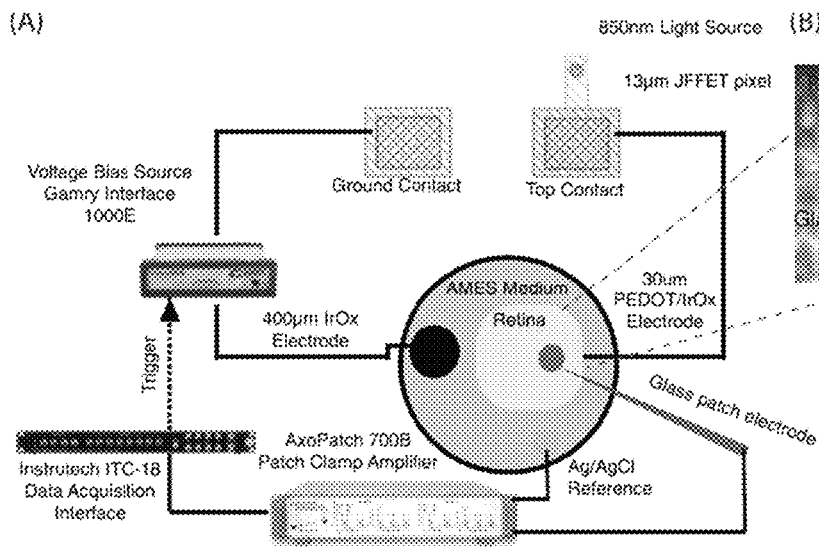
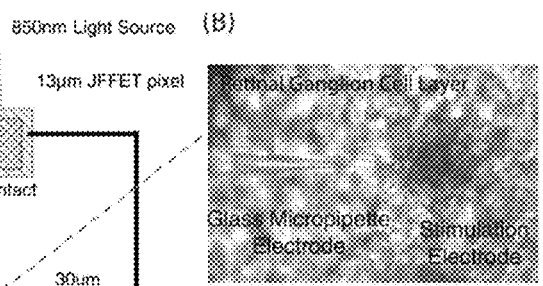
FIG. 5B
FIG. 5A
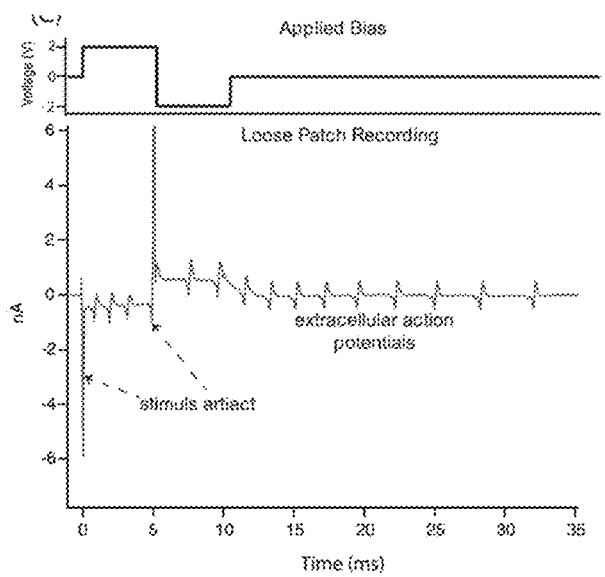
FIG. 5C
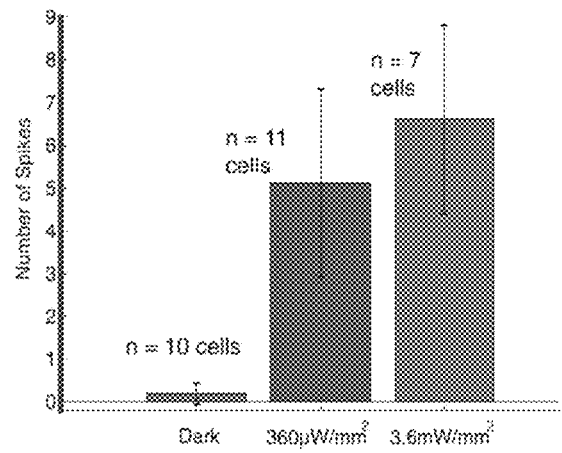
FIG. 5D

RETINAL PROSTHESES

This patent application claims priority to U.S. Provisional Patent Application Ser. No. 62/926,411, filed Oct. 25, 2019, the content of which is hereby incorporated by reference herein in its entirety into this disclosure.

BACKGROUND OF THE SUBJECT DISCLOSURE

Field of the Subject Disclosure

The present subject disclosure relates to retinal prostheses. More specifically, the present subject disclosure relates to retinal prostheses which include a single or array of photosensitive junction field-effect-transistors (Photo-JFET).

Background of the Subject Disclosure

Degenerative retinal diseases, including Retinitis Pigmentosa (RP) and Age-Related Macular Degeneration (AMD), are leading causes of blindness worldwide. Globally, about 1.5 million people (possibly 1 in 4000) are affected by RP and 50 million or more individuals suffer from AMD [1-3]. Patients with retinal degenerative diseases suffer from the selective loss of the photoreceptive cells of the retina, while the remaining retina remains intact. Retinal implants transduce visual information into current for neural stimulation with the goal of replacing lost photoreceptor function in patients blinded by degenerative diseases. These implants, known as retinal prostheses, aim to reestablish high acuity central vision with sufficiently large visual field without compromising any residual functional areas of the retina [4].

In general, a retinal prosthesis consists of a pixelated image sensor, a stimulation encoder, an array of neural stimulation electrodes, and a power supply. One category of retinal implant utilizes a head mounted camera to capture the visual scene that is relayed by a wireless inductive link to an implanted microprocessor. The microprocessor encodes the visual scene and relays necessary neural stimulation parameters to an array of directly wired stimulation electrodes implanted in close proximity to retinal neurons [5]. A prominent example of such a retinal implant is the Argus II Retinal Prosthesis (Second Sight Medical Technologies) which has received FDA approval (2014) and CE Mark (2011) to treat Retinitis Pigmentosa patients with bare or no light perception. The best visual acuity result in Argus II patients is on the order of 20/1260 [6,7].

Another category of retinal implant utilizes a directly implanted microphotodiode array (MPDA) to convert the spatiotemporal pattern of light impinging on the MPDA into electrical currents to stimulate the retina. However, the intensity of light under typical natural retinal irradiance (0.001-1 uW/mm$^2$) is orders of magnitude too low to be efficiently converted into electrical current for neural stimulation (μA) by a single photodiode [8,9]. Therefore, one approach of MPDA implants is to utilize a CMOS amplifier circuit within each pixel to amplify the primary photocurrent. An advantage of the CMOS approach is that the implant can encode spatiotemporal contrast across any typical visual scene without the need for externally worn imaging components [10,11]. The Alpha AMS/IMS system is an example of a MPDA CMOS retinal implant that has successfully received CE Mark. In clinical trials the Alpha AMS restored a best reported visual acuity nearing 20/546 [12,13]. A drawback to the CMOS approach, however, is the complexity of the required hardware that limits the fill factor and requires extensive encapsulation materials to electrically insulate the array and achieve biocompatibility [14].

An alternative MPDA retinal prosthetic approach is to use photodiodes and an external light source in the NIR wavelength to power and control the current produced by the array. Pulsed near infrared light is used to optically address the implanted photodiodes with sufficient irradiance to produce photocurrent for neural stimulation. This solution can greatly simplify the form factor of the implanted hardware by using only photodiodes operated in photovoltaic mode or as actively biased pixels sharing a common power line [8,15-17]. The prosthetic visual acuity of photodiode-only arrays is on the order of 20/200-20/400 [18]. However, a fundamental limitation of this approach is the high intensity of irradiating NIR light and the relatively large pixel area required for a photodiode to produce the necessary photocurrent to achieve neural stimulation. Stimulation of retinal neural cells requires electrical current pulses of 0.5-10 ms duration to deliver 1-100 nC of charge [19]. Typical silicon photodiodes have a light conversion efficacy less than 1 NW. This approach thus necessitates pixel diameters on the order of 40-100 μm and 5-25 mW/mm$^2$ of pulsed infrared light projected onto the eye, a power level close to the maximum permissible exposure of cornea and retina [15,20,21]. Therefore, there is inherently a tradeoff between minimizing pixel size to increase prosthesis resolution and the range of photocurrent to drive neural stimulation.

SUMMARY OF THE SUBJECT DISCLOSURE

To overcome the limitations of conventional retinal prosthetic systems, the present disclosure presents a photosensitive junction field-effect-transistor (Photo-JFET) that integrates a photodetector, amplifier, and neural electrode stimulator within a single silicon pixel mesa, thus achieving gain without sacrificing fill factor. Incorporating a gain mechanism into the body of a photo sensing pixel further advances existing retinal prostheses by enabling scaling of pixel size down to 10-20 μm to achieve improved visual acuity over existing optoelectronic prostheses. A vertically integrated Photo-JFET pixel is provided that can produce a broad range of current (0.1-100 μA) for robust retinal neural stimulation within a safe range of NIR irradiance with the potential to restore high acuity vision for the smallest reported retinal prosthesis pixel size, with the potential to achieve a prosthetic visual acuity of around 20/60 within a safe range of NIR irradiance.

In one exemplary embodiment, the present subject disclosure is a retinal prosthesis. The retinal prosthesis includes a vertically integrated photosensitive junction field-effect-transistor (Photo-JFET); and a neural stimulating electrode.

In another exemplary embodiment, the present subject disclosure is a retinal prosthesis. The retinal prosthesis includes a vertically integrated photosensitive junction field-effect-transistor (Photo-JFET) having a silicon pixel mesa; and a neural stimulating electrode; wherein a current range of 0.1-100 μA is produced.

In yet another exemplary embodiment, the present subject disclosure is a retinal prosthesis. The retinal prosthesis includes a vertically integrated photosensitive junction field-effect-transistor (Photo-JFET) having a silicon pixel mesa and a pixel size range of 1-100 μm; and a neural stimulating electrode.

BRIEF DESCRIPTION OF THE DRAWINGS

FIG. 5A shows a diagram of the circuit to connect Photo-JFET pixels on a chip to neural stimulation electrodes and the instrumentation used to record stimulated action potentials from retinal neurons, according to an exemplary embodiment of the present subject disclosure.

FIG. 5B shows a 10× microscope image of Rd10 retina atop of PEDOT/IrOx electrode on transparent substrate with a glass micropipette electrode used to loose patch RGC to record action potentials, according to an exemplary embodiment of the present subject disclosure.

FIG. 5C shows spiking behavior recorded from RGC in response to electrical stimulation driven by Photo-JFET pixels, according to an exemplary embodiment of the present subject disclosure.

FIG. 5D shows comparison of spikes elicited by Photo-JFET stimulation under dark and NIR illumination, according to an exemplary embodiment of the present subject disclosure.

DETAILED DESCRIPTION OF THE SUBJECT DISCLOSURE

The present subject disclosure addresses the shortcomings of conventional retinal prostheses by providing vertically integrated photo-JFET pixel architectures and methods of use.

1. Design of Photo-JFET Pixel Architecture for Retinal Prosthesis

Figure 1A:
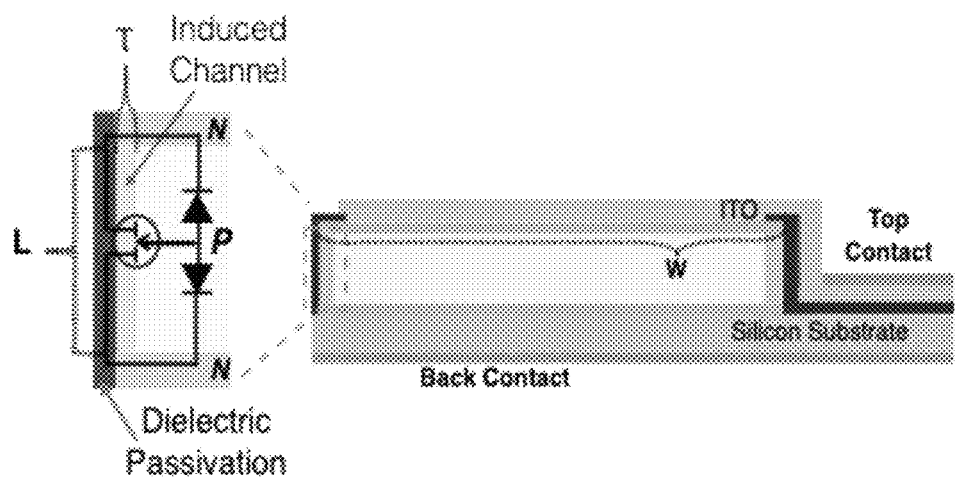
FIG. 1A shows a Photo-JFET pixel from a vertical etched mesa, according to an exemplary embodiment of the present subject disclosure.
Figure 1B:
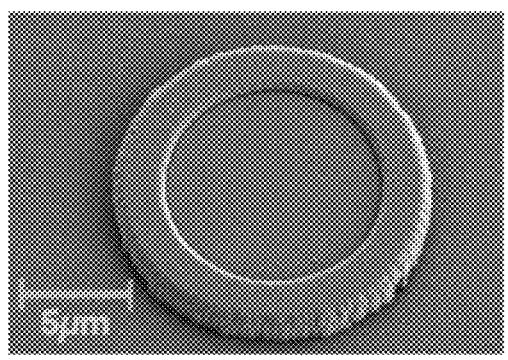
FIG. 1B shows a scanning electron microscope micrograph (SEM) of a 13 μm Photo-JFET single pixel test structure, according to an exemplary embodiment of the present subject disclosure.

As shown in FIG. 1A, a vertically integrated Photo-JFET pixel may include a pair of back-to-back p/n diodes in parallel with a sidewall junction field-effect-transistor. The diodes can be configured in either a N—P—N or P—N—P configuration for a n-channel or p-channel JFET. A dielectric film is deposited on the sidewall of the silicon mesa to induce a weak inversion layer along the vertical edge of the middle layer of the back-to-back diode, forming a vertical channel along the mesa sidewall. Silicon dioxide ($SiO_2$) or aluminum oxide ($Al_2O_3$), or other applicable material, may be used to control the pinch-off voltage of the sidewall JFET. A voltage bias applied across the top and bottom diodes can provide drain-source voltage ($V_{DS}$) for the Photo-JFET, and the same voltage also provides reverse and forward bias of two back-to-back p/n junctions. The diode orientation can be reversed by changing the polarity of the source-drain bias. The Photo-JFET is normally off in the dark and can be turned on by incident light. Here the doping profile and thickness of the vertical N—P—N (or P—N—P) structure are designed in such a way that the structure does not perform as a regular bipolar transistor (i.e., the current gain of the bipolar structure $h_{fe} \ll 1$). Instead, the structure can be modeled as 2 back-to-back P/N diodes, and the only transistor function is provided by the sidewall JFET.

Referring more specifically now to FIGS. 1A-1D, FIG. 1A shows the design of a Photo-JFET pixel from a vertical etched mesa. A dielectric passivation layer deposited on the sidewall of the silicon mesa induces a channel along the vertical wall of the middle layer of the mesa. The sidewall view illustrates the pair of back-to-back p/n diodes and the junction field-effect-transistor (JFET) realized as an NPN or PNP stack.

Figure 2A:
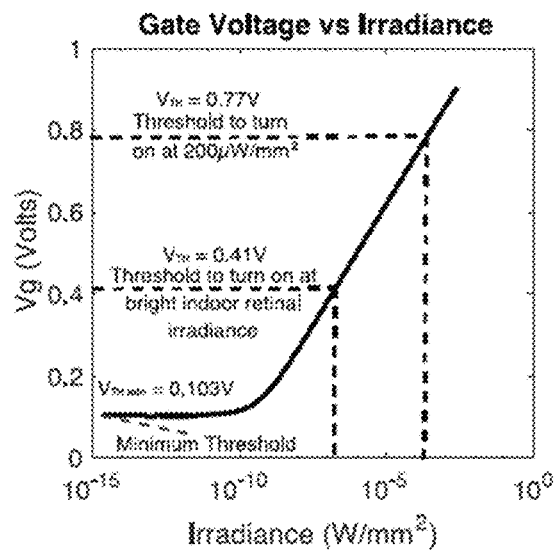
FIG. 2A shows a theoretical performance characteristics of a vertical silicon Photo-JFET using typical device parameters for a range of retinal irradiance, calculated gate to source voltage ($V_{GS}$) for a range of irradiance conditions following Eq. (1), according to an exemplary embodiment of the present subject disclosure.
Figure 2B:
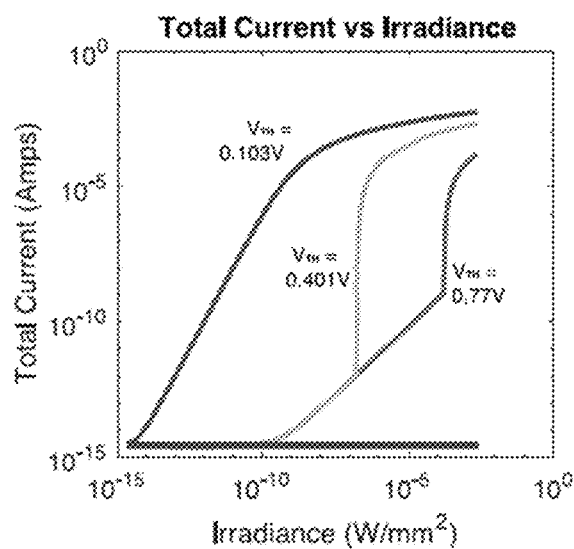
FIG. 2B shows calculated total current ($I_{Tot}$) using the identified threshold voltages in FIG. 2A, according to an exemplary embodiment of the present subject disclosure.

FIG. 2B shows a scanning electron microscope micrograph (SEM) of a 13 μm Photo-JFET single pixel test structure. The mesa sidewall and outer rim are coated in $SiO_2$ layer while electrical contact is made through a center opening in the passivation.

Figure 1C:
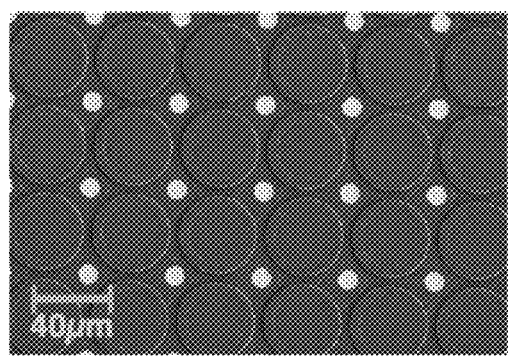
FIG. 1C shows a SEM micrograph of prototype array with 40 μm pixels paired with 10 μm electrodes (light gray) spaced at 45 μm pitch, a theoretical prosthetic acuity of 20/188, according to an exemplary embodiment of the present subject disclosure.

FIG. 1C shows an SEM micrograph of prototype array with 40 μm pixels paired with 10 μm electrodes (light gray) spaced at 45 μm pitch, having a theoretical prosthetic acuity of 20/188.

Figure 1D:
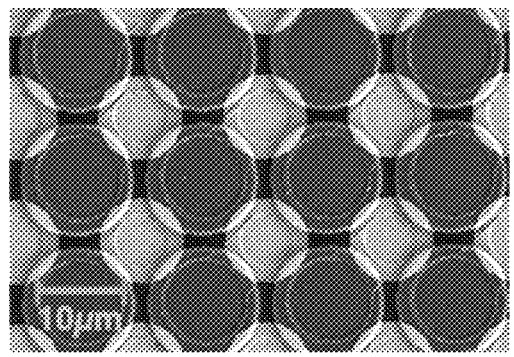
FIG. 1D shows a SEM micrograph of prototype array with 13 μm pixels paired with 10 μm electrodes (light gray) spaced at 15 μm pitch, a theoretical acuity of 20/60, according to an exemplary embodiment of the present subject disclosure.

FIG. 1D shows an SEM micrograph of prototype array with 13 μm pixels paired with 10 μm electrodes (light gray) spaced at 15 μm pitch, having a theoretical acuity of 20/60.

Although the examples shown above and in the figures have specific dimensions, other dimensions are also possible and within the purview of one having skill in the art after consideration of the present subject disclosure. For example, pixel sizes of 13 μm and 40 μm have been used throughout this disclosure as an example. However, the JFET architecture can be recognized in any size from 1-100 μm. Optionally, groups of pixels can be operated as a single unit with a shared neural stimulating electrode. Such variations are within the scope of the present disclosure.

1.1 Operation Principle

Under illumination the reverse biased p/n diode produces a photocurrent ($I_{ph}$). Both the photocurrent ($I_{ph}$) and the reverse saturation current ($I_{o1}$) flow through the forward biased p/n junction, modulating the voltage across this forward-biased diode according to the Shockley diode model:

$$V_{GS} = \eta V_T \ln\left(1 + \frac{I_{o1} + I_{ph}}{I_{o2}}\right) \quad (1)$$

where η is the ideality factor, $V_T$ is the thermal voltage, and $I_{o2}$ is the reverse saturation current for the forward biased p/n junction. Note that in this design, $V_{GS}$ in Eqn. (1) is not only the voltage drop across the forward-biased p/n junction but also the gate-to-source voltage of the JFET. In an ideal design, the threshold voltage required ($V_{THmin}$) to turn on the normally-off JFET will be greater than the $V_{GS}$ produced by dark current ($I_{o1}$) but low enough such that the channel will turn on at low irradiance (Eqn. (2) for a N-channel JFET).

The actual threshold voltage of the JFET depends on the doping of the middle p-doped region for the N—P—N configuration and the dielectric-silicon mesa interface. For a retinal prosthesis, a Photo-JFET can be engineered with high $V_{TH}$ and operated by optical addressing with NIR irradiance to control contrast and adjust the range of available photocurrent to the correct range for neural stimulation. FIG. 2A demonstrates the range of possible $V_{GS}$ calculated for lighting conditions spanning a range from retinal irradiance under dim lighting conditions to the typical irradiance of supplemental NIR light used in retinal prostheses as described above.

$$V_{TH\ min} = \eta V_T \ln\left(1 + \frac{I_{o1}}{I_{o2}}\right) \quad (2)$$

1.2 Photocurrent Calculation

With sufficient illumination the $V_{GS}$ will exceed the threshold voltage ($V_{TH}$) to turn on the JFET and modulate the drain current ($I_D$) across the channel. The drain current in the saturation region for a normally-off N-channel JFET can be represented by Eqn. (3) where W is the effective channel width, equal to the circumference of the mesa, L is the length of the vertical channel, a is the effective channel width controlled by the thickness of charge inversion layer at the oxide-silicon mesa sidewall interface. The net output current in response to the input light is the sum of the original primary photocurrent across the back-to-back p/n junctions ($I_{ph}$) and the drain current ($I_D$) through the sidewall JFET.

$$I_D = \frac{W\mu\varepsilon_s}{2La}(V_{GS} - V_{TH})^2 \quad (3)$$

Combining Eqns. (1) and (3) and under the condition that the photocurrent is much greater than the reverse saturation current Io1, the drain current of the sidewall JFET represented by Eqn. (4) is obtained when the JFET is in saturation region.

$$I_D = \frac{W\mu\varepsilon_s}{2La}\left[\eta V_T \ln\left(1 + \frac{I_{ph}}{I_{o2}}\right) - V_{TH}\right]^2 \quad (4)$$

The total current produced by a Photo-JFET pixel under illumination is the sum of the drain current and the primary photocurrent (Eqn. (5)). The total current can be several orders of magnitude greater than the primary photocurrent produced by the photodiode layer. The dependence of the total current on the threshold voltage of a Photo-JFET calculated for a typical device dimension is shown in FIG. 2.

$$I_{Total} = I_D + I_{ph} + I_{o1} \quad (5)$$

Assuming that the voltage threshold is greater than $V_{GS\ Dark}$, the total current produced in the dark condition is equivalent to the reverse saturation current, $I_{o1}$, of the reverse biased diode (Eqn. (6)). In practice, the actual reverse bias leakage current will likely be much higher than the theoretical value and will increase with the reverse bias voltage. However, as shown in FIG. 2B, the $V_{TH}$ of the Photo-JFET can be carefully engineered to achieve a photocurrent to dark current ratio between 10-10,000 depending upon the required intensity of irradiating light to turn on the JFET channel.

$$I_{TotalDark} = I_{o1} \quad (6)$$

When the illuminating irradiance generates sufficient $V_{GS}$ to exceed $V_{TH}$, the current versus irradiance curve shifts abruptly from a simple linear current-irradiance relationship, as expected for a photodiode, to a regime where the current level rises several orders of magnitude with increasing irradiance. The dark current level remains flat as long as the $V_{GS}$ in dark is below the ideal minimum threshold $V_{TH}$. This rapid rise in current results from the phototransistive gain achieved by a Photo-JFET pixel, $G_{JFET}$, which can be formulated as the ratio of the total current in Eq. 5 to the current from the reverse biased photodiode when illuminated (Eqn. (7)).

$$G_{JFET} = \frac{I_{Total}}{I_{ph} + I_{o1}} \quad (7)$$

Figure 2C:
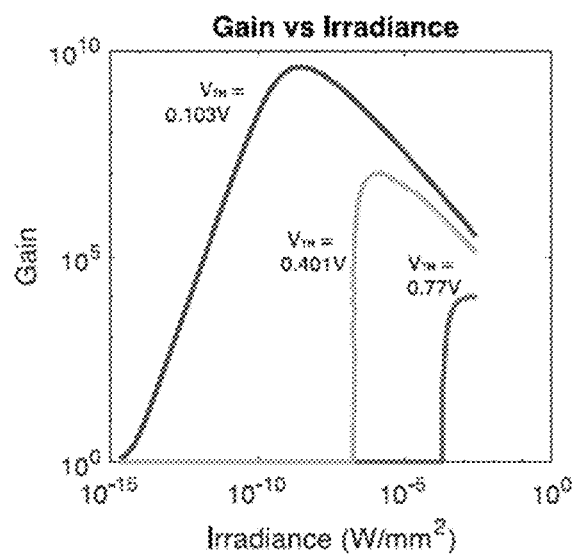
FIG. 2C shows calculated gain achieved over the irradiance range, according to an exemplary embodiment of the present subject disclosure.

When $V_{GS} > V_{TH}$ the gain quickly increases before reaching a peak level after which the gain decreases with increasing irradiance due to the channel current saturation of the JFET (FIG. 2C). Although in the JFET saturation regime the gain decreases with increasing irradiance, the total current still increases monotonically with the irradiance in a fashion similar to the natural retinal response, thus extending the dynamic range of the retinal prosthesis.

FIG. 2. Shows a theoretical performance characteristics of a vertical silicon Photo-JFET using typical device parameters for a range of retinal irradiance.

FIG. 2A shows calculated gate to source voltage ($V_{GS}$) for a range of irradiance conditions following Eqn. (1). Marked on the graph are the possible values of the threshold voltage to turn on the JFET channel for ideal case of minimum threshold, bright indoor retinal irradiance, and 200 μW/mm² supplemented NIR.

FIG. 2B shows calculated total current ($I_{Tot}$) using the identified threshold voltages in FIG. 2A. FIG. 2C shows calculated gain achieved over the irradiance range. For simplicity, the subthreshold current in FIG. 2B-2C have been ignored, thus underestimating the total current and gain in subthreshold regime.

1.3 Neural Stimulation

The total current produced at the Photo-JFET pixel is delivered to retinal tissue through a stimulation electrode in contact with the top of the silicon mesa (FIGS. 1C-1D). For a N—P—N device, anodic stimulation current will be produced by applying positive bias to the top N layer and cathodic stimulation current will be produced by reversing the polarity of bias voltage. Each individual pixel in a retinal prosthesis implant must produce sufficient current to independently stimulate a region of retinal neural cells. The present subject disclosure is not limited to a single pixel but can be an array. The required output current per pixel to reach half-maximal effective stimulation with 10-30 μm diameter stimulation electrodes is reported to be between 1.8-7 µA based on in vitro studies [19]. Furthermore, the stimulation threshold for individual cells within a single retina may vary due to differences in the morphology and phenotype, as well as the actual distance between stimulating electrodes and target cells over the entire span of an implanted array. Therefore, the total current produced by a Photo-JFET pixel must reach a level of ~10 uA for a safe range of NIR irradiance while the $V_{TH}$ of the JFET-channel must be sufficiently high such that the dark current will never inadvertently result in stimulation.

2 Fabrication

A Photo-JFET device structure, according to the present subject disclosure, was realized by microfabrication techniques in a class 100 cleanroom facility. Single pixel test structures for device characterization (FIG. 1B) and array prototypes (FIGS. 1C and 1D) were formed by etching silicon mesas from an epitaxially grown wafer with doped sequential N—P—N layers on a N+ substrate. For in vitro testing, single pixel test structures were interfaced with neural stimulation electrodes fabricated on borosilicate glass discs. This transparent electrode substrate served as the bottom of the recording chamber to allow visualization of retinal neurons with differential interference microscopy for physiological recordings.

3.1 Device Fabrication

Pixel mesas were fabricated at 13 µm and 40 µm diameter using a deep reactive ion etching and inductively coupled plasma process to a height of 1.5 µm, to form the back-to-back diode structure. A dielectric layer of $SiO_2$ was deposited by plasma enhanced chemical vapor deposition over the entire mesa to create a weak inversion layer along the height of the P—Si layer, thereby forming a vertical FET along the mesa sidewall. An opening was etched in the $SiO_2$ dielectric on top of the silicon mesa and an ITO layer was deposited over it to form a transparent electrical contact. For single pixel test structures, a gold contact pad was deposited on top of the ITO layer off the pixel to allow for probing. A common ground contact shared by each pixel was formed by depositing a gold layer on the back of the device substrate. Pixels in the array prototype were finished with a 10 µm diameter iridium oxide electrode on top of the ITO layer in the space between adjacent mesas.

2.2 Stimulation Electrode Fabrication

Briefly, electrodes for in vitro retinal stimulation were fabricated by depositing transparent conductive traces of Indium Tin Oxide (ITO) on a borosilicate glass disc. Traces were electrically insulated by a layer of SiNx deposited by plasma enhanced vapor deposition. A hole was etched through the SiNx layer to expose the ITO-electrode contact using reactive ion etching. Iridium oxide electrodes of 30 µm diameter were deposited over each opening by reactive DC sputtering of an Iridium metal target in an Argon (90%) and Oxygen (10%) gas mixture at a thickness of 600 nm. Finally, a layer of Polyethylenedioxythiophene/Polysulfostyrene (PEDOT/PSS) was deposited on top of the iridium oxide electrode from 0.01 M EDOT in 2.5 g per 100 mL NaPSS (Sigma-Aldrich) by galvanostatic electrodeposition at a fixed current density of 5 mA/cm² for 10 seconds in phosphate buffered saline versus an Ag/AgCl electrode. A 400 µm diameter iridium oxide was also fabricated on the periphery of the glass disc to serve as the return electrode.

3. Measured Optoelectronic Performance of Photo-JFET Pixels

Figure 3:
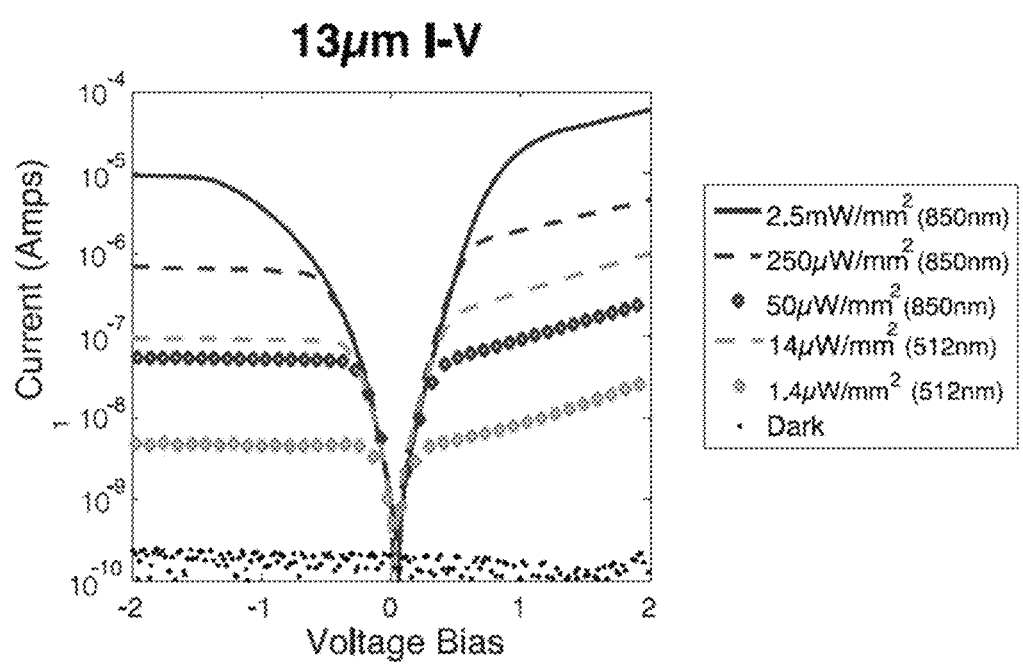
FIG. 3 shows I-V Characteristics of Photo-JFET pixels for 13 μm diameter pixels under illumination with visible (518 nm) and NIR (850 nm) light, according to an exemplary embodiment of the present subject disclosure.

FIG. 3 shows I-V characteristics of Photo-JFET pixels for 13 µm diameter pixels under illumination with visible (518 nm) and NIR (850 nm) light.

The current-voltage characteristics of Photo-JFET pixels were measured under voltage bias and illumination (FIG. 3). Visible light (518 nm) and NIR (850 nm) were used to investigate device photoresponse. A uniform laser spot of 60 µm diameter was projected using a 10× plan infinity corrected long working distance objective (Mitutoyo #46-144) onto all devices so that each pixel diameter was evaluated under the same irradiance conditions. A source meter (Keysight B2900A) was used to sweep the voltage bias from –2V to 2V at 50 mV/s and measure the total current across the silicon mesa.

Both photosensitive regions are sensitive to visible (518 nm) and NIR (850 nm) light (FIG. 3). The I-V characteristic is slightly asymmetric at equivalent voltage bias of opposite polarity. The bias polarity across the silicon mesa dictates which region of the NPN stack is reverse biased and thus photosensitive. With positive bias the primary photosensor is the top diode, whereas with negative bias it is the bottom diode. The asymmetry of the photoresponse with voltage bias polarity can be explained by the difference in absorption coefficient of both wavelengths in the top and bottom diodes. Overall, the Photo-JFET pixels have better photoresponse at 518 nm than 850 nm wavelength light. This difference in photoresponse can be explained by the difference in relative absorption length of the two wavelengths within the 1.5 µm height of the silicon mesa, which favors the absorption of shorter wavelength light in the photosensing region of the Photo-JFET. The 40 µm pixel devices possess similar I-V characteristics to 13 µm pixel devices at equivalent incident light power.

The "turn on" characteristic of the normally-off JFET is dictated by the current output from the primary photo sensing diode that is used to modulate the gate-to-source voltage, $V_{GS}$, as described above. The Photo-JFET is in the saturation regime with its current modeled by Eqn. (3) when $|V_{DS}|>1V$). At $|V_{DS}|=1.5V$, the dark current for 13 µm diameter pixel devices is well below the neural excitation threshold of ~1 µA.

Illumination of the Photo-JFET with 518 nm or 880 nm light causes the JFET channel to turn on. With sufficient illuminating irradiance, the total current produced by the Photo-JFET pixel is orders of magnitude higher than the primary photocurrent produced by a reverse biased photodiode (FIG. 3). At low irradiance of <10 uW/mm², the photoresponsivity is less than 1 NW, equivalent to a simple photodiode. However, as the light power increases, the effective responsivity rises to 100 A/W with voltage bias (FIG. 4). The required irradiance of 850 nm light to turn on the JFET channel is around 50 uW/mm² for a 13 µm pixel and 8 uW/mm² for a 40 µm pixel. Both 13 µm and 40 µm Photo-JFET pixels have similar performance in terms of photoresponsivity. For both devices, gain reaches the peak value then decreases with increasing irradiance, in agreement with the device model.

Figure 4A:
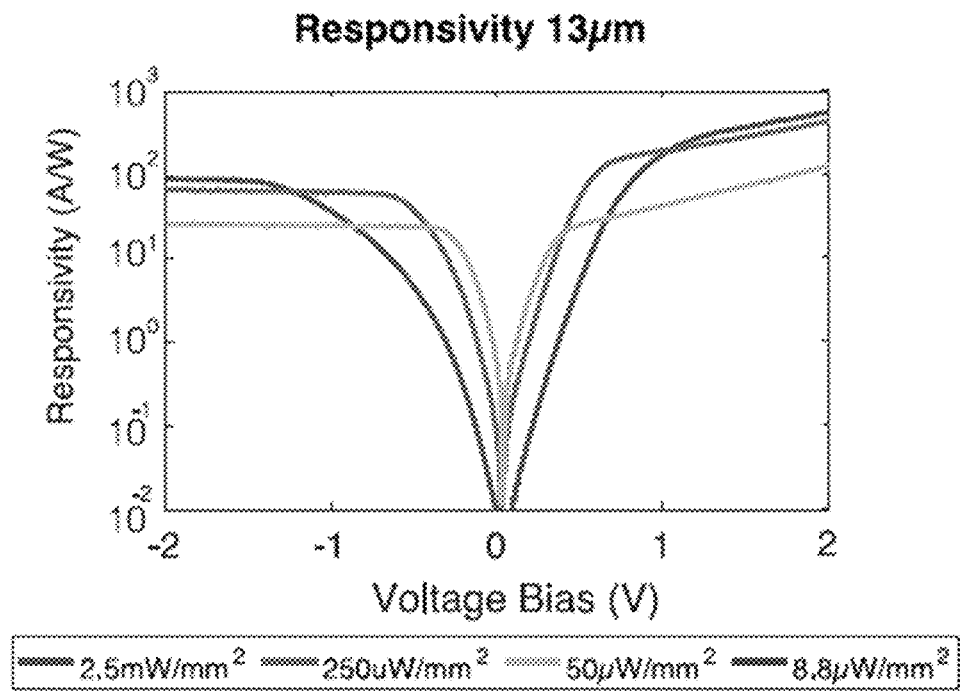
FIG. 4A shows voltage dependence of responsivity for NIR illumination (850 nm) of a 13 μm photo-JFET pixel, according to an exemplary embodiment of the present subject disclosure.
Figure 4B:
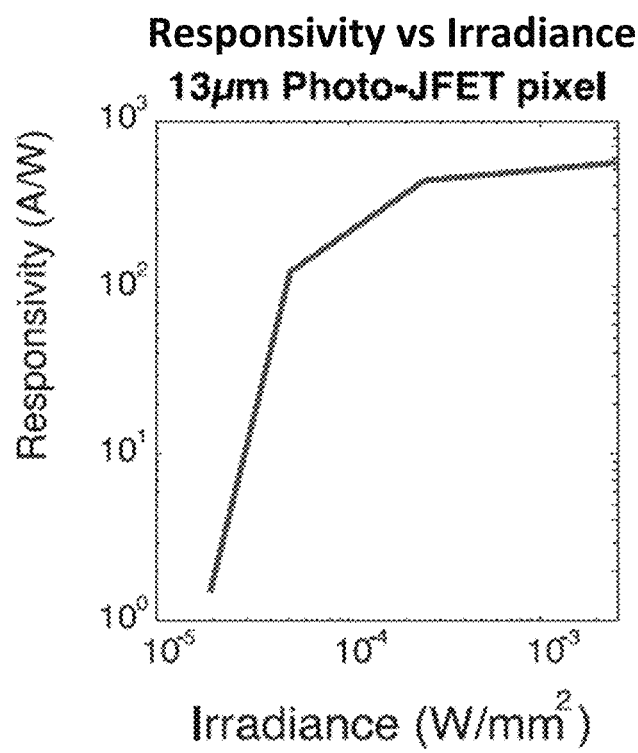
FIG. 4B shows responsivity of a 13 μm diameter pixel vs. NIR irradiance (850 nm) at 2V bias, according to an exemplary embodiment of the present subject disclosure.

More specifically, FIG. 4A shows voltage dependence of responsivity of a 13 µm photo-JFET pixel and FIG. 4B shows Responsivity of a 13 µm diameter pixel vs. NIR irradiance at 2V bias.

4. Utility of Photo-JFET Pixels for Retinal Prosthesis

To investigate how a Photo-JFET pixel can evoke neural stimulation, an ex vivo retinal stimulation strategy was devised. All experimental methods and animal care procedures were approved by the University of California San Diego Institutional Animal Care and Use Committee. Adult rd10 mice (>P60) with photoreceptor cell degeneration were anesthetized with isoflurane and euthanized by decapitation and their retinas were isolated and maintained in Ames medium oxygenated and equilibrated with 95% $O_2$, 5% $CO_2$. 2 mm×2 mm retina pieces were transferred to a recording chamber with a glass bottom with the fabricated stimulating electrodes on an upright microscope and perfused with Ames solution (4 ml/min) at 35° C. Retina was placed over stimulating electrodes ganglion cell side up. Retinal ganglion cells (RGCs) were visualized using IR differential interference contrast video microscopy. Recording electrodes were pulled from borosilicate capillary glass to have a final resistance of 4-5 MS) and filled with Ames medium. Action potentials in RGCs were recorded in the loose patch configuration using a Multiclamp 700b (Molecular Devices). Signals were filtered at 4 kHz (4-pole Bessel), digitized at 20 kHz with an ITC-18 (HEKA Electronik) and saved to a PC for offline analysis.

Electrical probes were used to connect the contact pads of the 13 µm Photo-JFET test structure to a single 30 µm stimulation electrode underneath ganglion cells targeted for recording and a distant 400 µm return electrode on the glass disc. An isolated voltage source (Gamry Interface1000E) was used to provide bias across the entire circuit as represented in FIG. 5A. The pixel mesa was illuminated with a 60 µm spot of NIR light (850 nm) using the method described above at irradiance levels expected to achieve sufficient photocurrent to exceed an expected stimulation threshold of ~1 µA based on measured I-V performance. Bias was applied to the circuit for 5 ms at +2V (anodal) followed by 5 ms at −2V (cathodal) while the pixel was kept dark or illuminated (360 µW/mm² or 3.6 mW/mm²). RGC action potentials were observed and counted within the first 40 ms following the onset of the stimulus. Each stimulation condition was repeated for 10 consecutive trials separated by 9 seconds and spike counts were averaged for each cell.

Under voltage bias and illumination with NIR light, a single Photo-JFET pixel produced sufficient photocurrent to trigger action potentials in RGCs at both irradiance conditions. The dark current produced at 2V bias elicits negligible spiking activity, on the order of spontaneous firing in RGC. With an average of 5.1 and 6.6 spikes at 360 µW/mm² and 3.6 mW/mm² respectively, there are significantly more action potentials for both illumination conditions versus the 0.19 spikes observed in dark ($p<0.0001$, paired t-test). While more spikes are observed at 3.6 mW/mm² ($p<0.005$, paired t-test) the 10× increase in irradiance only corresponds to a 30% increase in elicited action potentials.

FIG. 5 shows an overview of the in vitro experiment to demonstrate retinal stimulation with Photo-JFET pixels.

FIG. 5A shows a diagram of the circuit to connect Photo-JFET pixels on chip to neural stimulation electrodes and the instrumentation used to record stimulated action potentials from retinal neurons. FIG. 5B shows a 10× microscope image of Rd10 retina atop of PEDOT/IrOx electrode on transparent substrate with a glass micropipette electrode used to loose patch RGC to record action potentials. FIG. 5C shows spiking behavior recorded from RGC in response to electrical stimulation driven by Photo-JFET pixels. FIG. 5D shows a comparison of spikes elicited by Photo-JFET stimulation under dark and NIR illumination, with in vitro retinal stimulation with 13 µm Photo-JFET pixel at 360 µW/mm² and 3.6 mW/mm².

5. Discussion

A novel architecture has been proposed consisting of a vertical photo-junction field-effect-transistor for optoelectronic retinal implants. The Photo-JFET design combines the functions of light sensing and gain that addresses the critical design goal for retinal prosthesis of minimizing pixel size to enable high visual acuity. The design was successfully realized by microfabrication of silicon Photo-JFET pixels of 13 µm and 40 µm diameter. The device photoresponse was measured under visible and NIR irradiance and demonstrating characteristic JFET gain behavior (FIG. 3). The measured FET photoresponsivity (FIG. 4B) corresponded with the calculated theoretical gain behavior for representative pixel size (FIG. 2C). The optimal parameters for voltage biasing and NIR irradiance that produce current in the desired range of >1 µA for neural stimulation were identified. The utility of Photo-JFET pixels for retinal prosthesis were validated with in vitro experiments whereby an optically addressed 13 µm pixel successfully stimulated retinal neurons. Therefore, an optically addressed photo-JFET approach enables use of the smallest reported pixel size for neural stimulation in a retinal prosthesis implant.

Figure 6:
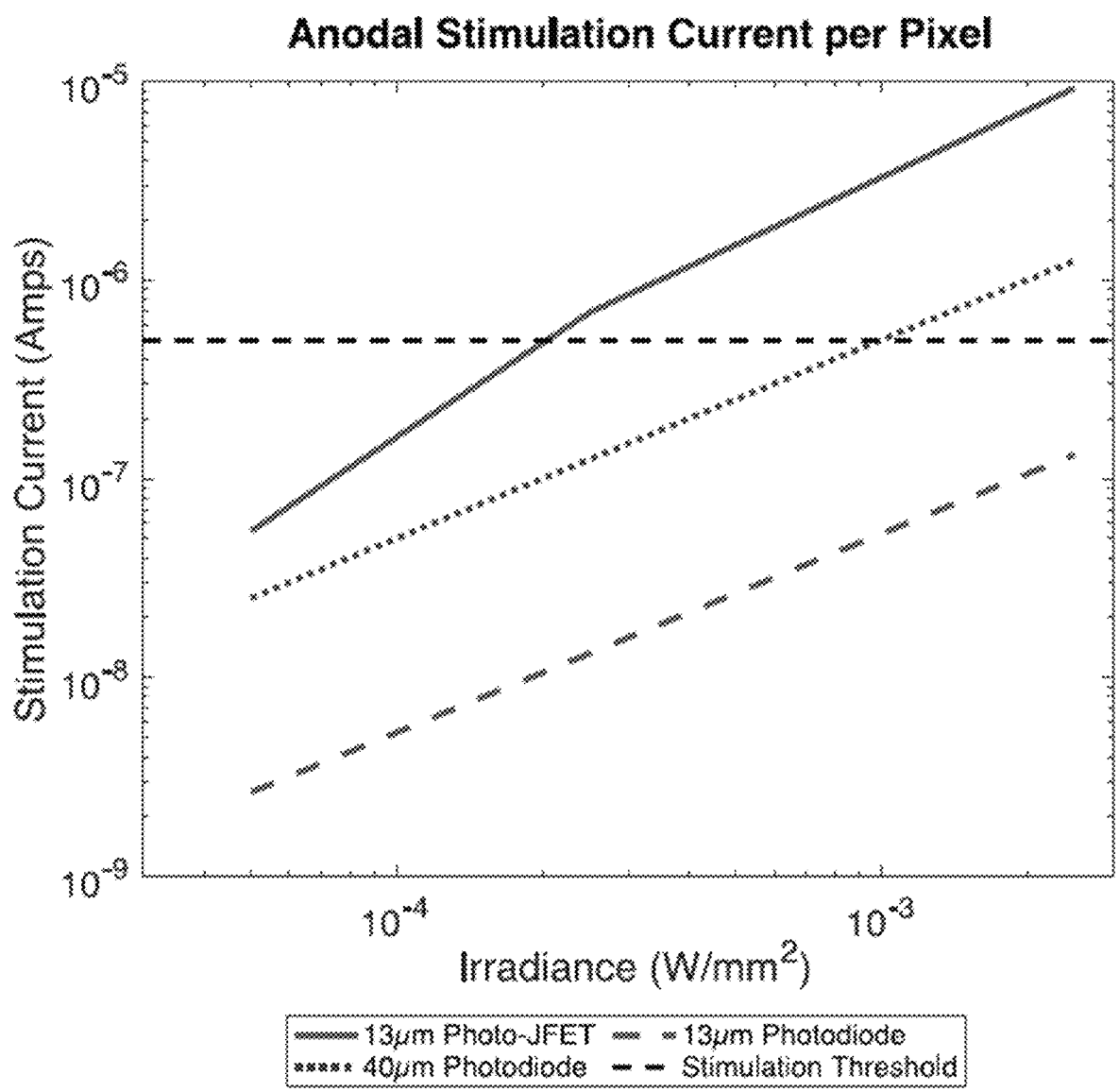
FIG. 6 shows a comparison of measured current produced by 13 μm Photo-JFET pixels versus theoretical current of passive photodiode pixels at 13 μm and 40 μm diameter under the same illumination conditions with NIR light (850 nm), according to an exemplary embodiment of the present subject disclosure.

While Photo-JFET pixels are responsive to visible light, the irradiance of visible light required (>14 µW/mm²) for sufficient retinal stimulation current is well outside the range of typical retinal irradiance and the safe exposure limit of 518 nm light. Therefore, similar to existing technologies, a NIR source can be used to optically address Photo-JFET array to encode stimulation parameters such as stimulation current and spatial contrast [8,16]. The maximum permissible irradiance of 850 nm on the cornea and lens is 200 µW/mm² for continuous exposure over 8 hours and 5.9 mW/mm² for 5 ms of pulsed exposure at 20 Hz repetition [23,24]. Based on the in vitro proof-of-concept results, a 13 µm pixel can effectively stimulate retinal neural cells within the safety limits of NIR exposure at 360 µW/mm². Using reported stimulation thresholds as a guideline, Photo-JFET pixels can produce sufficient current for stimulation within a safe range of NIR light at 850 nm (FIG. 6). Alternatively, devices can be optically addressed with less NIR irradiance if the pixel size is expanded. Photo-JFET devices produce similar total output current at equivalent incident light power since the performance is proportional to pixel circumference and primary photocurrent (Eqn. (4)). At the cost of prosthetic acuity, larger Photo-JFET devices can also produce sufficient current for neural stimulation at much lower NIR irradiance than similarly sized MPDA pixels.

The spatial resolution of a retinal prosthesis is determined by the center-to-center electrode spacing in the array. Specifically, for an implantable MPDA, electrode spacing depends directly on the photosensing area required per individual pixel to produce sufficient current for stimulation. The reported minimum current required to stimulate a retinal neuron in vitro with microelectrodes is ~500 nA for anodic-first stimulation and slightly higher at ~800 nA for cathodic-first at 10 ms pulse duration. [22]. A 13 µm Photo-JFET pixel can utilize phototransistive gain to produce enough current beyond threshold for neural stimulation (FIG. 6). Whereas, a photodiode only approach requires larger pixel of at least 40 µm and NIR light nearing maximum permissible exposure (MPE) to reach stimulation threshold. On this basis, a Photo-JFET pixel-based prosthesis may achieve higher spatial resolution beyond that of existing MPDA technologies.

It is noted that while the best theoretical restorable visual acuity is determined by the electrode pitch, electrochemical crosstalk will determine the actual spatial resolution of the array. Crosstalk arises from overlapping signals from adjacent electrodes due to the spread of current density in an ionic environment. A closer apposition of the stimulating electrode to the retinal neural tissue can lower stimulation threshold and help preserve the spatial resolution of a high-density array. Given the simplicity of the device structure and fabrication, a Photo-JFET array can be modified to mitigate the effect of crosstalk. For example, the silicon mesa comprising the Photo-JFET pixel can be etched from the epitaxial silicon substrate to form a micropillar with a vertical height on the order of 10-50 μm.

In the United States the criteria for legal blindness is visual acuity worse than 20/200 or a visual field less than 20°. A clinically meaningful retinal prosthesis for AMD patients must restore high acuity central vision on the order of 20/100 or better to enable reading of large font. Previous studies of MPDA devices have demonstrated successful retinal neural stimulation in clinical experiments. However, the measured prosthetic visual acuity in human patients was typically quite low, below 20/540 [12,13]. The Photo-JFET approach described herein allows for the smallest reported pixel size used for an optoelectronic retinal prosthesis by vertically integrating a gain mechanism within the body of the photosensor. An implantable version of the Photo-JFET prosthesis may consist of an array of pixels on silicon die attached to a flexible polymer substrate, connected via an inductive link to an external power source to supply the voltage bias. Photo-JFET pixels of 13 μm diameter can be arrayed at 15 μm pitch, enabling a prosthetic spatial resolution of ~20/60 which may offer a substantial improvement in clinical visual acuity for patients with degenerative retinal disease.

FIG. 6 shows a comparison of measured current produced by 13 μm Photo-JFET pixels versus theoretical current of passive photodiode pixels at 13 μm and 40 μm diameter under the same illumination conditions with NIR light (850 nm). A responsivity of 0.4 NW is assumed for passive photodiodes [25].

Conclusions

A novel vertical junction field-effect-transistor architecture has been developed that achieves photosensing, gain, and neural stimulation in a compact pixel size for high visual acuity retinal prosthesis. The design was realized by a vertically integrated back-to-back diode structure in parallel with a sidewall FET. Photo-JFET pixels were successfully fabricated at pixel dimensions approaching cellular scale. A simple bias mechanism and optical addressing using NIR light produce a broad range current for neural stimulation per pixel. It was demonstrated in a proof-of-concept experiment that a single Photo-JFET pixel can effectively stimulate retinal neurons in an in vitro model of degenerative retinal disease. The Photo-JFET design allows for smaller pixel sizes with improved functionality versus passive microphotodiode arrays. This subject disclosure demonstrates an important development towards high visual acuity retinal prostheses that may help restore clinically meaningful vision, better than 20/100 in patients with degenerative retinal disease.

This application incorporates by reference herein in its entirety the publication: Damle et al., "Vertically integrated photo junction-field-effect transistor pixels for retinal prosthesis," Biomedical Optics Express (11)1, 55-67 (January 2020).

This application further incorporates by reference herein in their entirety all of the following cited references, which disclose various findings as discussed in the present disclosure:

1. K. Ganesan, A. Stacey, H. Meffin, S. Lichter, U. Greferath, E. L. Fletcher, and S. Prawer, "Diamond penetrating electrode array for Epi-Retinal prosthesis," 2010 Annu. Int. Conf. IEEE Eng. Med. Biol. Soc. EMBC'10 (March), 6757-6760 (2010).
2. T. Flores, X. Lei, T. Huang, H. Lorach, R. Dalal, L. Galambos, T. Kamins, K. Mathieson, and D. Palanker, "Optimization of pillar electrodes in subretinal prosthesis for enhanced proximity to target neurons," J. Neural Eng. 15(3), aaac39 (2018).
3. L. Yue, J. D. Weiland, B. Roska, and M. S. Humayun, "Retinal stimulation strategies to restore vision: Fundamentals and systems," Prog. Retin. Eye Res. 53, 21-47 (2016).
4. G. A. Goetz and D. V Palanker, "Electronic approaches to restoration of sight.," Rep. Prog. Phys. 79(9), 096701 (2016).
5. J. D. Weiland and M. S. Humayun, "Retinal prosthesis," IEEE Trans. Biomed. Eng. 61(5), 1412-1424 (2014).
6. L. da Cruz, J. D. Dorn, M. S. Humayun, G. Dagnelie, J. Handa, P. O. Barale, J. A. Sahel, P. E. Stanga, F. Hafezi, A. B. Safran, J. Salzmann, A. Santos, D. Birch, R. Spencer, A. V. Cideciyan, E. de Juan, J. L. Duncan, D. Eliott, A. Fawzi, L. C. Olmos de Koo, A. C. Ho, G. Brown, J. Haller, C. Regillo, L. V. Del Priore, A. Arditi, and R. J. Greenberg, "Five-Year Safety and Performance Results from the Argus II Retinal Prosthesis System Clinical Trial," Ophthalmology 123(10), 2248-2254 (2016).
7. M. S. Humayun, J. D. Dorn, L. Da Cruz, G. Dagnelie, J. A. Sahel, P. E. Stanga, A. V. Cideciyan, J. L. Duncan, D. Eliott, E. Filley, A. C. Ho, A. Santos, A. B. Safran, A. Arditi, L. V. Del Priore, and R. J. Greenberg, "Interim results from the international trial of second sight's visual prosthesis," Ophthalmology (2012).
8. D. Palanker, A. Vankov, P. Huie, and S. Baccus, "Design of a high-resolution optoelectronic retinal prosthesis," in *Journal of Neural Engineering* (2005), 2(1).
9. Y. T. Yang, P. K. Lin, C. Wan, W. C. Yang, L. J. Lin, C. Y. Wu, and C. C. Chiao, "Responses of rabbit retinal ganglion cells to subretinal electrical stimulation using a silicon-based microphotodiode array," Investig. Ophthalmol. Vis. Sci. 52(13), 9353-9361 (2011).
10. K. Stingl, K. U. Bartz-Schmidt, D. Besch, A. Braun, A. Bruckmann, F. Gekeler, U. Greppmaier, S. Hipp, G. Hortdorfer, C. Kernstock, A. Koitschev, A. Kusnyerik, H. Sachs, A. Schatz, K. T. Stingl, T. Peters, B. Wilhelm, and E. Zrenner, "Artificial vision with wirelessly powered subretinal electronic implant alpha-IMS," Proc. R. Soc. B Biol. Sci. (2013).
11. C. L. Lee and C. C. Hsieh, "A 0.8-V 4096-pixel CMOS sense-and-stimulus imager for retinal prosthesis," IEEE Trans. Electron Devices (2013).
12. K. Stingl, K. U. Bartz-Schmidt, D. Besch, C. K. Chee, C. L. Cottriall, F. Gekeler, M. Groppe, T. L. Jackson, R. E. MacLaren, A. Koitschev, A. Kusnyerik, J. Neffendorf, J. Nemeth, M. A. N. Naeem, T. Peters, J. D. Ramsden, H. Sachs, A. Simpson, M. S. Singh, B. Wilhelm, D. Wong, and E. Zrenner, "Subretinal Visual Implant Alpha IMS—Clinical trial interim report," Vision Res. 111, 149-160 (2015).
13. T. L. Edwards, C. L. Cottriall, K. Xue, M. P. Simunovic, J. D. Ramsden, E. Zrenner, and R. E. MacLaren, "Assessment of the Electronic Retinal Implant Alpha AMS in Restoring Vision to Blind Patients with End-Stage Retinitis Pigmentosa," Ophthalmology 125(3), 432-443 (2018).
14. R. Daschner, U. Greppmaier, M. Kokelmann, S. Rudorf, R. Rudorf, S. Schleehauf, and W. G. Wrobel, "Laboratory and clinical reliability of conformally coated subretinal implants," Biomed. Microdevices 19(1), 1-8 (2017).

15. D. Boinagrov, X. Lei, G. Goetz, T. I. Kamins, K. Mathieson, L. Galambos, J. S. Harris, and D. Palanker, "Photovoltaic Pixels for Neural Stimulation: Circuit Models and Performance," IEEE Trans. Biomed. Circuits Syst. 10(1), 85-97 (2016).
16. S. Ha, M. L. Khraiche, A. Akinin, Y. Jing, S. Damle, Y. Kuang, S. Bauchner, Y.-H. Lo, W. R. Freeman, G. A. Silva, and G. Cauwenberghs, "Towards high-resolution retinal prostheses with direct optical addressing and inductive telemetry.," J. Neural Eng. 13(5), 056008 (2016).
17. B. Bosse, S. Damle, A. Akinin, Y. Jing, D. U. Bartsch, L. Cheng, N. Oesch, Y. H. Lo, G. Cauwenberghs, and W. R. Freeman, "In vivo photovoltaic performance of a silicon nanowire photodiode-based retinal prosthesis," Investig. Ophthalmol. Vis. Sci. (2018).
18. H. Lorach, G. Goetz, R. Smith, X. Lei, Y. Mandel, T. Kamins, K. Mathieson, P. Huie, J. Harris, A. Sher, and D. Palanker, "Photovoltaic restoration of sight with high visual acuity," Nat. Med. 21(5), 476-482 (2015).
19. A. Coma, T. Herrmann, and G. Zeck, "Electrode-size dependent thresholds in subretinal neuroprosthetic stimulation," J. Neural Eng. 15(4), (2018).
20. J. D. Loudin, D. M. Simanovskii, K. Vijayraghavan, C. K. Sramek, A. F. Butterwick, P. Huie, G. Y. McLean, and D. V Palanker, "Optoelectronic retinal prosthesis: system design and performance.," J. Neural Eng. 4(1), S72-84 (2007).
21. H. Lorach, J. Wang, D. Y. Lee, R. Dalal, P. Huie, and D. Palanker, "Retinal safety of near infrared radiation in photovoltaic restoration of sight," Biomed. Opt. Express 7(1), 13-21 (2016).
22. D. Boinagrov, S. Pangratz-Fuehrer, G. Goetz, and D. Palanker, "Selectivity of direct and network-mediated stimulation of the retinal ganglion cells with epi-, sub- and intraretinal electrodes," J. Neural Eng. 11(2), (2014).
23. D. Sliney, D. Aron-Rosa, F. DeLori, F. Fankhauser, R. Landry, M. Mainster, J. Marshall, B. Rassow, B. Stuck, S. Trokel, T. M. West, and M. Wolffe, "Adjustment of guidelines for exposure of the eye to optical radiation from ocular instruments: statement from a task group of the International Commission on Non-Ionizing Radiation Protection (ICNIRP).," Appl. Opt. 44(11), 2162-76 (2005).
24. ANSI, *American National Standard for Safe Use of Lasers* (2014), ANSI Z136.
25. J. D. Loudin, D. M. Simanovskii, K. Vijayraghavan, C. K. Sramek, A. F. Butterwick, P. Huie, G. Y. McLean, and D. V. Palanker, "Optoelectronic retinal prosthesis: System design and performance," J. Neural Eng. 4(1), (2007).

The foregoing disclosure of the exemplary embodiments of the present subject disclosure has been presented for purposes of illustration and description. It is not intended to be exhaustive or to limit the subject disclosure to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Further, in describing representative embodiments of the present subject disclosure, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written, and one skilled in the art can readily appreciate that the sequences may be varied and still remain within the spirit and scope of the present subject disclosure.

What is claimed is:

1. A retinal prosthesis, comprising:
a vertically integrated photosensitive junction field-effect-transistor (Photo-JFET) etched from a silicon substrate doped to form a stack of N—P—N or P—N—P layers, forming a silicon mesa pillar and having an outer wall which is coated with a dielectric layer of SiO2, which induces an inversion layer along a vertical direction on the outer wall of the silicon mesa; and
a neural stimulating electrode.

2. The retinal prosthesis in claim 1, wherein the Photo-JFET includes a photodetector.

3. The retinal prosthesis in claim 1, wherein the Photo-JFET includes an amplifier.

4. The retinal prosthesis in claim 1, wherein the Photo-JFET includes a neural electrode stimulator.

5. The retinal prosthesis in claim 1, wherein the Photo-JFET includes a silicon pixel mesa.

6. The retinal prosthesis in claim 5, wherein the silicon pixel mesa further includes a photodetector.

7. The retinal prosthesis in claim 6, wherein the silicon pixel mesa further includes an amplifier.

8. The retinal prosthesis in claim 7, wherein the silicon pixel mesa further includes a neural electrode stimulator.

9. The retinal prosthesis in claim 8, further comprising a dielectric film positioned on the silicon pixel mesa.

10. The retinal prosthesis in claim 1, wherein a current range of 0.1-100 µA is produced by the retinal prosthesis when illuminated with near infrared light at an irradiance of 0.01-5 mW/mm$^2$.

11. The retinal prosthesis in claim 1, further comprising a 13 µm pixel.

12. The retinal prosthesis in claim 1, further comprising an array of 13 µm pixels.

13. The retinal prosthesis in claim 1, further comprising a 40 µm pixel.

14. The retinal prosthesis in claim 1, further comprising an array of 40 µm pixels.

15. The retinal prosthesis in claim 1, further comprising a pair of back-to-back p/n diodes.

16. The retinal prosthesis in claim 15, wherein the diodes are configured in a N—P—N configuration.

17. The retinal prosthesis in claim 15, wherein the diodes are configured in a P—N—P configuration.

18. A retinal prosthesis, comprising:
a vertically integrated photosensitive junction field-effect-transistor (Photo-JFET) etched from a silicon substrate doped to form a stack of N—P—N or P—N—P layers, forming a silicon mesa pillar and having an outer wall which is coated with a dielectric layer of SiO2, which induces an inversion layer along a vertical direction on the outer wall of the silicon mesa; and
a neural stimulating electrode;
wherein a current range of 0.1-100 µA is produced when illuminated with near infrared light at an irradiance of 0.01-5 mW/mm$^2$.

19. A retinal prosthesis, comprising:
a vertically integrated photosensitive junction field-effect-transistor (Photo-JFET) having a pixel size range of 1-100 μm and etched from a silicon substrate doped to form a stack of N—P—N or P—N—P layers, forming a silicon mesa pillar and having an outer wall which is coated with a dielectric layer of SiO2, which induces an inversion layer along a vertical direction on the outer wall of the silicon mesa; and
a neural stimulating electrode.

20. The retinal prosthesis in claim 19, further comprising an array of pixel size range of 1-100 μm.

* * * * *